United States Patent [19]

Schweitzer

[11] 4,336,722
[45] Jun. 29, 1982

[54] METHOD AND APPARATUS FOR SAMPLING WASTE GASES

[75] Inventor: Ernest D. Schweitzer, Saanichton, Canada

[73] Assignee: Candel Industries, Limited, Victoria, Canada

[21] Appl. No.: 203,935

[22] Filed: Nov. 4, 1980

[51] Int. Cl.³ .............................................. G01N 1/14
[52] U.S. Cl. ................................................ 73/863.12
[58] Field of Search ........................ 73/863.11, 863.12

[56] References Cited

U.S. PATENT DOCUMENTS

| | | | |
|---|---|---|---|
| 2,895,335 | 7/1959 | Kraftson | 73/421.5 |
| 2,987,921 | 6/1961 | Kraftson | 73/421.5 |
| 3,593,023 | 7/1971 | Dodson | 73/863.12 |
| 3,611,812 | 10/1971 | Cleveland | 73/421.5 R |
| 4,191,541 | 3/1980 | Jenkins | 55/18 |
| 4,211,116 | 6/1980 | Pilat et al. | 73/421.5 A |

Primary Examiner—S. Clement Swisher
Attorney, Agent, or Firm—Townsend and Townsend

[57] ABSTRACT

A method and apparatus for continuously withdrawing a gas sub-sample from a chamber enclosing a source of waste gas for introduction of the sub-sample to a gas monitor. The method includes withdrawing a sample of the waste gas from the chamber by use of a vacuum source located exterior to the chamber. From the latter sample a sub-sample of waste gas is extracted prior to the waste gas entering the vacuum source. The sub-sample is then cooled below the ambient dew point so that condensate contained in the sub-sample is separated from the latter. The cooled sub-sample is then directed to a gas monitor for analysis of the gaseous components contained in the latter.

18 Claims, 2 Drawing Figures

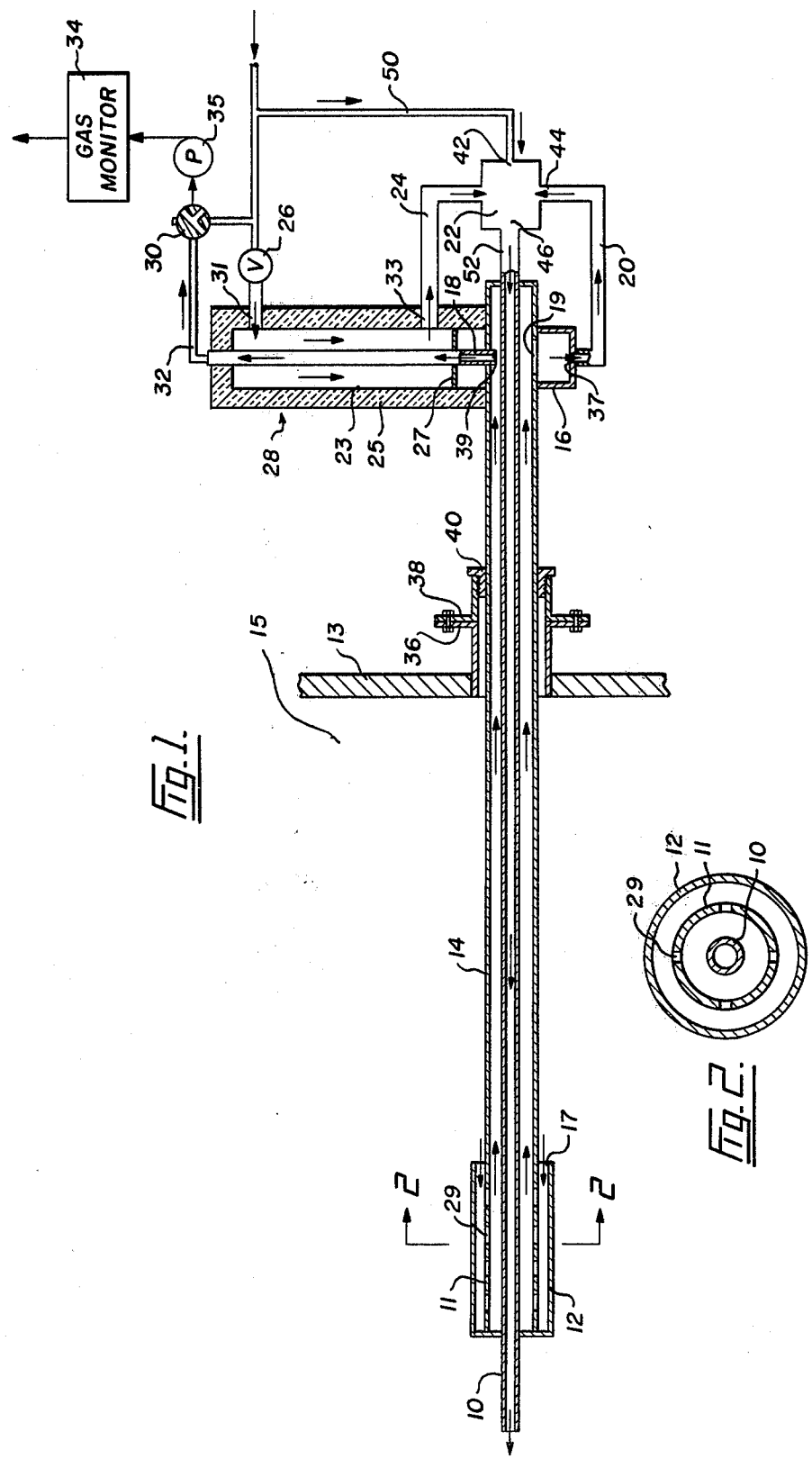

METHOD AND APPARATUS FOR SAMPLING WASTE GASES

BACKGROUND OF THE INVENTION

The present invention relates to a method and apparatus for continuously withdrawing from waste gases containing particulate matter, moisture and condensates, a clean gas sample for use in monitoring or analysis.

Waste gases which are produced from industrial processes such as chemical recovery boilers, waste incinerators etc. contain chemicals and combustion products which when released into the atmosphere pollute the environment. Control and optimizing of these processes in order to obtain a desirable balance of combustion products and waste gases is achieved by sampling of the waste gas and analysis of the gaseous components contained therein, preferably on a continuous basis. Known methods of withdrawing gaseous samples from such waste gases encounter problems in dealing with the particulate matter, moisture and condensate vapours which clog and corrode the sampling apparatus. In addition the condensates present may be carried over with the gas sample to foul monitoring or analysis apparatus or render the gas sample incomplete by absorption of part or all of the gas sample constituents to be monitored or analyzed. Ideally, a sampling apparatus should deliver an intact gas sample representative of the source atmosphere and having a free flowing rate sufficient so that when it is monitored it reflects the process parameters as the system is operating and at the time of monitoring or analysis. In addition, the sampling apparatus itself should be constructed of a material or combination of materials which will resist corrosion by the source atmosphere and gas sample such that maintenance of the gas sampling probe is significantly reduced or eliminated. Some known methods of continuously withdrawing a gas sample from a source of waste gas have employed a high velocity jet of steam for aspiration of sample gases through a probe and for driving the resultant steam-gas mixture into a chamber where water is added to the steam-gas mixture to condense the steam about the foreign matter in the gas sample. The resultant foreign matter whose effective mass is increased by the condensed steam is separated from the gas to be analyzed by a centrifugal separator. Using water in this way results in the formation of corrosive liquids which can attack the sampling apparatus. The water also affects the contents of gaseous components by introducing into the sample gas oxygen from the water and dissolving $CO_2$, $SO_2$, $H_2S$, $NO_x$ and other components of interest from the gas sample in the water.

SUMMARY OF THE INVENTION

According to the present invention there is provided apparatus for continuously withdrawing a gas sub-sample from a chamber enclosing a source of waste gas for introduction of the sub-sample to a gas monitor. The apparatus includes a sample probe tube having an inlet located within the source chamber and a gas passageway from the inlet to an exit region exterior to the chamber. A baffle located at the inlet deflects and a probe inlet filters out particulate matter present in the source gas prior to entering the sample probe tube. An aspirator having an aspirating gas inlet, an exhaust outlet axially aligned and oppositely disposed with respect to the aspirating gas inlet and a return line inlet is used to create a vacuum for withdrawing a sample of the waste gas from the source chamber. A sump line couples the exit region of the sample probe tube to the aspirator sump line inlet. An outlet housing which defines a passageway from the exhaust outlet of the aspirator to the interior of said chamber is used for conducting excess sample gas and aspirator gas back to the source of waste gas in the waste gas chamber for subsequent conduction to the atmosphere. A sub-sample tube defines a gas sub-sample passageway which communicates with the exit region and which conducts a portion of the source gas sub-sample through a cooling chamber to the gas monitor such that the sub-sample is cooled below the ambient dew point and resulting condensate falls back into the return tube and is conducted to the aspirator and along the outlet housing to the interior of the chamber.

Advantageously the apparatus further comprises an aspirator gas conducting line for coupling to a pressurized source of aspirator gas and to the aspirator. The pressurized reducing valve is inserted in the aspirator gas conducting line and is used to reduce aspirator gas pressure to achieve the adiabatic cooling of same. An adiabatic cooling chamber surrounds the sub-sample flow line and has an inlet connected to the outlet of the pressure reducing valve and an outlet for connection to the aspirator gas conducting line.

Preferably the apparatus further includes a means for directing the flow of aspirator gas through the sub-sample tube, the sump line, said return line, the sample probe tube and probe inlet in a reverse direction for purging the latter-mentioned tubes and inlet of accumulated particulate matter.

Corrosion problems are largely avoided by utilizing a corrosive resistant material such as titanium, hastalloy (trade mark) or inconel (trade mark) of the sample probe tube, the baffle, the sub-sample tube, the return line and the aspirator gas conducting line. The aspirator is preferably also made of non-corrosive material such as that selected from the group consisting of stainless steel, tetrafluoroethylene, or polyvinyl chloride.

In another aspect of the invention there is provided a method for continuously withdrawing a gas sub-sample from a chamber enclosing a source of waste gas for subsequent introduction of the sub-sample to a gas monitor. The method includes withdrawing a sample of the waste gas from the chamber by use of a vacuum source exterior to the chamber. From the flow of waste gas there is extracted a sub-sample of the sample of waste gas prior to the waste gas entering the vacuum source. Condensate is then removed from the sub-sample by cooling the latter below its dew point. By directing the cooled sub-sample to a gas monitor, analysis of the gaseous components of the sub-sample is thereby achieved without interference of particulate matter, condensate or gaseous components introduced in preparing the sub-sample.

Particulate matter may be removed from the sample gas by filtering it prior to extraction of the sub-sample.

Preferably, the vacuum source is an aspirator and the vacuum is created by passing an aspirating gas through the aspirator.

Advantageously, the method further includes conducting the gas sample and aspirating gas emerging from the aspirator back into the waste gas chamber in order to permit the former to be exhausted to the atmosphere together with the waste gas.

The aspirating gas may be adiabatically expanded and used to cool the sub-sample prior to the sub-sample entering the aspirator.

Additionally, by directing the aspirating gas prior to expansion into a sub-sample tube which conducts the sub-sample and from there into a sample probe tube which conducts the sample from the chamber and then out through the probe inlet, a purging of the aforesaid tubes and the inlet of accumulated particulate matter is achieved.

The method and apparatus permits the extraction of a representative sample of the waste gas on a continuous basis at a point close to the initial source of extraction of the waste gas sample without introduction into the sub-sample extracted of contaminating media such as water, steam or aspirating gas. Consequently, a sub-sample is obtained which is accurately representative of the waste gas being monitored and is available for analysis with a minimum of time lag between its time of extraction and the time in which it is introduced into the gas monitor.

By utilizing non-corrosive material such as titanium, stainless steel, tetrafluoroethylene, or polyvinyl chloride for the various parts in contact with the waste gas, corrosion of the sampling apparatus is largely avoided. Provision for use of the aspirator gas in periodic repurging the tubes and probe inlet of the sampling apparatus of particulative matter provides for efficient use of the aspirator gas. The periodic purging of the apparatus results in a self-cleaning mechanism which eliminates the need to shut down the process being monitored in order to clean the sampling apparatus.

BRIEF DESCRIPTION OF THE DRAWINGS

In drawings illustrating a preferred embodiment of the invention,

FIG. 1 is a cross-sectional view of the gas sampling apparatus as installed in the walls of a chamber enclosing waste gas, and FIG. 2 is a cross-sectional view taken along the line 2—2 shown in FIG. 1.

DESCRIPTION OF THE PREFERRED EMBODIMENTS

The general construction of the gas sampling apparatus and its method of installation is illustrated in FIG. 1. Here a tubular excess sample return tube line 10 extends from the interior of the waste gas chamber 15 through a wall 13 enclosing same to an exhaust outlet 46 of an aspirator 22. Concentrically disposed with respect to the return tube 10 is a sample probe tube 14 which terminates in the interior of the chamber 15 in a cylindrical probe inlet 11. The probe inlet consists of a plurality of perforations 29 proximate the end of the probe tube 14 of a sufficiently small size to filter particulate matter from the waste gas. The probe inlet 11 is enclosed within a cylindrical baffle 12 which, in turn, is sealed to the sample probe 14 and concentrically disposed therewith. The diameter of the baffle 12 is slightly larger than that of the sample probe tube 14 thus providing an annular opening 17 leading into the area of the probe inlet 11. The passageway defined by the area between the sample probe tube 14 and the excess sample return tube 10 defines a passageway for a sample of waste gas obtained from the chamber 15. At the opposite end of the sample probe tube 10 there is an exit region whereat there is joined to the sample probe tube 14 a small vertical sub-sample tube 18. The lower end of the sub-sample tube 18 defines a sub-sample outlet 39 which extends within the gas passageway of the sub-sample probe tube 14. A hole 19 in the sample probe tube 14 located generally below the sub-sample outlet 39 allows the gas passageway of the sub-sample probe tube 14 to communicate with the interior of a sump reservoir 16. The sump reservoir 16 is mounted to the sample probe tube 14 so that it encloses the excess gas outlet hole 19. Concentrically enclosing the sub-sample tube 18 and also mounted to the sample probe tube 14 at its lower end is an adiabatic cooling chamber 28 which is comprised of an inner cylindrical housing 23 around which is a preselected thickness of urethane foam insulation 25. The cylindrical housing is closed at its bottom by an end plate 27 sealed to both the outer wall of the sub-sample tube 18 and the inner wall of the cylindrical housing 23. Coupled to a cooling gas inlet 31 of the cylindrical housing 23 is the outlet of a pressure reducing valve 26. The inlet of the pressure reducing valve 26 is coupled to a source of compressed air (not shown). The bottom of the cylindrical housing 23 contains a cooling gas outlet 33 which is coupled by means of a cooling gas line 24 to an aspirator 22. An aspirator pressure line 50 couples an aspirator gas inlet 42 directly to a source of pressurized aspirator gas (not shown).

The sub-sample tube 18 is joined at its top to a sub-sample conducting line 32 which couples the sub-sample tube 18 to a third port of a three way valve 30. An inlet port of the three way valve is coupled to the source of compressed air (not shown) while the outlet port is coupled to a pump 35. The output of the pump 35 is coupled to a gas monitor 34.

A sump outlet 37 at the bottom of the sump reservoir 16 is coupled by a sump line 20 to an excess gas inlet 44 of the aspirator. An exhaust gas outlet 46 of the aspirator 22 is coupled by an exhaust line 52 to the excess sample return tube 10. The entire gas sample assembly is fitted to a wall 13 of the chamber 15 by means of a flanged tube 36 attached to the wall, a floating flanged tubular section 38 threaded on its interior surface which a threadedly receives a cylindrical flanged plug 40 tightly fitted around the sample probe tube 14. Bolts through the mating flanges of the flanged tube member 36 and the floating flanged tubular section 38 in conjunction with the plug 40 hold the assembly in place.

FIG. 2 shows a section taken along the line 2—2 of FIG. 1.

In operation waste gas from within chamber 15 diffuses through the sample gas inlet 17 and passes through the probe inlet 11 before entering the gas passageway of the sample probe tube 14 in response to a vacuum created in the gas passageway of the sample probe tube 14 by the aspirator 22. The sample gas flows along the gas passageway of the sample probe tube 14 toward an exit region of the sample probe tube 14. The portion of the gas sample diffuses through a sub-sample inlet 39 into a sub-sample tube 18. The remaining excess gas flows out the excess gas outlet hole 19 into the interior of a sump reservoir 16 and then out through the sump outlet 37 along the sump line 20 into the aspirator 22. As the sub-sample gas flows upwardly through the sub-sample tube, 18 it passes through the interior of the adiabatic cooling chamber 28 where it is cooled below the ambient dew point so that any condensate falls back down the sub-sample tube 18 and is flushed by the sample gas flow in the sample probe tube 14 out through the sump reservoir 16. The resultant cooled sub-sample gas continues its flow out of the cooling chamber 28 through the sub-sample tube 18 along a sub-sample conducting line 32 through a three-way valve 30 and into a pump 35. The pump 35 conveys the clean sub-sample to a gas monitor 34. In order to operate the cooling chamber 28 a source of compressed air (not shown) is passed through a pressure reducing valve 26 which causes an output flow at a reduced pressure. The expanded air enters the cylindrical housing 23 through the cooling gas inlet 31 where it flows down around the sub-sample tube 18 and out the bottom of the cylindrical housing 23 through a cooling gas outlet 33. The same cooled gas is conducted by the cooling gas line 24 into the aspirator 22. Compressed air from a source (not shown) flows along pressure line 50 to the aspirator gas inlet 42 of the aspirator 22 and creates a vacuum in the aspirator which draws the waste gas into the gas passageway of the sample probe line 14 and out through the sump reservoir 16 into the excess gas inlet 44 of the aspirator 22. From time to time accumulated particulate matter in the system may be purged by manual operation of the three-way valve 30 which closes off the flow to the pump 35 and connects the sub-sample conducting line 32 to the source of compressed air.

The pressure drop across the throttling valve required in order to result in a cooling of the sub-sample gas below the ambient dew point is typically 50 to 70 lbs. per square inch. The probe inlet 11 prevents excessive particulate capture and plugging of the probe assembly. Instead of a manually operated three-way valve 30 a solenoid operated three-way valve may be used.

Instead of directing the cooled air emerging from the cooling gas outlet 33 into the aspirator 22 it may be coupled to the exhaust line 52 or to the sump line 20. Alternatively, the cooling gas outlet 33 could be coupled to the aspirator gas inlet 42 in place of the pressure line 50 and used to create a vacuum for withdrawing the sample of waste gas.

Other departures, variations and modifications which do not depart from the spirit of the invention nor the scope as defined in the appended claims will be obvious to those skilled in the art.

I claim:

1. Apparatus for continuously withdrawing a gas sub-sample from a waste gas chamber enclosing a source of waste gas for introduction of the sub-sample to a gas monitor, comprising:
   (a) a sample probe tube having a sample gas probe inlet located within said chamber and a gas passageway extending from the probe inlet to an exit region exterior to said chamber for continuously withdrawing a sample of said waste gas, said probe inlet for filtering out particulate matter present in the waste gas;
   (b) a baffle located proximate the sample gas inlet for deflecting particulate matter present in the waste gas;
   (c) an aspirator having an aspirating gas inlet for coupling to a source of aspirating gas, an exhaust outlet and a sump line inlet;
   (d) a sump line connected to said exit region and extending to the aspirator sump line inlet for conducting gas flowing through the exit region to the aspirator;
   (e) a return tube extending from said aspirator exhaust outlet to the interior of said waste gas chamber for conducting excess sample gas and aspirator gas thereto;
   (f) a sub-sample tube connected to the exit region at one end and couplable at its other end to a gas monitor; and
   (g) an adiabatic cooling chamber having a cooling gas inlet and outlet, said chamber enclosing at least a portion of said sub-sample tube for cooling sub-sample gas therein below the ambient dew point so that resultant condensate from the sub-sample gas falls back into the flow of sample gas and is conducted thereby to the aspirator and then out through said return tube into said waste gas chamber.

2. Apparatus as defined in claim 1, further comprising:
   (a) means for adiabatically expanding a said pressurized source of aspirator gas;
   (b) coupling means for coupling expanded aspirator gas to said cooling gas inlet of said chamber for cooling said sub-sample tube below the ambient dew point, and
   (c) means for discharging said expanded aspirator gas from said chamber.

3. Apparatus as defined in claim 2, further comprising means for selectively directing a flow of pressurized gas in a reverse direction through said sub-sample tube and said gas passageway of said sample probe tube for purging the sump line, aspirator, said return tube, their associated inlets and outlets and said baffle of accumulated particulate matter.

4. Apparatus as defined in claim 3, wherein said sample probe tube, said probe inlet, said baffle, said sub-sample tube, said sump line and a line coupling the aspirator to said cooling chamber and said aspirator are of a corrosion resistant material.

5. Apparatus as defined in claim 3, wherein said directing means is a three way valve positioned in the coupling line between the outlet of said sub-sample tube and the gas monitor having a port for coupling to a pressurized source of aspirator gas whereby a flow of pressurized aspirator gas may be directed in a reverse direction through said sub-sample tube.

6. Apparatus as defined in claims 1, 2 or 4, wherein said aspirator gas is air.

7. Apparatus for continuously withdrawing a gas sub-sample from a chamber containing a source of waste gas for introduction of the sub-sample to a gas monitor, comprising:
   (a) a sample probe tube extending through a wall of said waste gas chamber, said tube having a probe inlet at an end within said chamber for continuously receiving a sample of said waste gas and a sub-sample outlet and an excess gas return outlet at the opposite end of said tube exterior to said waste gas chamber, said probe inlet also for filtering out particulate matter from said waste gas sample;
   (b) a baffle covering the inlet of said sample probe tube for deflecting particulate matter from waste gas flowing therethrough;
   (c) an excess gas return tube concentric with said sample probe tube and having a smaller diameter than the latter, the space between said sample probe tube and return tube defining a sample gas passageway, and the interior of said return tube being a return conduit for excess gas and condensate to said waste gas chamber;
   (d) a cylindrical baffle concentric with and having a larger diameter than said sample probe tube, said baffle enclosing said probe inlet and sealed at one end to said excess gas return tube proximate an end of the latter such that said baffle extends away from the end of said return tube to an open end, the open end of said baffle together with said probe tube defining an entrance aperture to said baffle;

(e) means for connecting said sample probe tube to said waste gas chamber wall;

(f) an adiabatic cooling chamber having a cooling gas inlet and a cooling gas outlet;

(g) a sub-sample tube at least a portion of which is enclosed by said cooling chamber, said tube being connected to the sub-sample outlet for withdrawing a sub-sample of said sample of waste gas whereby said sub-sample is cooled by said adiabatic cooling chamber below the ambient dew point so that resulting condensate in said sub-sample goes back in a reverse direction through said sub-sample tube into said excess gas return tube and be subsequently flushed out through the excess gas return outlet;

(h) a sump reservoir below said return outlet having a sump outlet at the bottom thereof for receiving excess gas and condensate from said gas passageway of said sample probe tube;

(i) an aspirator having an aspirator gas inlet coupled to a source of pressurized aspirator gas, an exhaust outlet axially aligned with said aspirator gas inlet and a sump line coupled to said aspirator intermediate said aspirator gas inlet and said exhaust outlet, said sump line coupled to the sump outlet;

(j) a pressure reducing valve couplable to a source of pressurized aspirator gas and having an output coupled to the cooling gas inlet of said cooling chamber for reducing the pressure of the aspirator gas prior to its flow into the cooling chamber;

(k) means for discharging cooling gas emerging from the cooling gas outlet into said return tube, (l) means for selectably directing a portion of pressurized aspirator gas from said source of aspirator gas in a reverse direction through said sub-sample tube for purging said sub-sample tube, said sample gas probe tube said probe inlet and said baffle of the accumulated particulate matter.

8. Apparatus as defined in claim 7 wherein said aspirator gas is air.

9. Apparatus as defined in claim 7, wherein said sample probe tube, said baffle, said sub-sample tube, said sump reservoir and said excess gas return tube and said aspirator are of a corrosion resistant material.

10. Apparatus as defined in claims 7, 8 or 9, wherein said means for directing aspirator gas flow is a three-way valve having one inlet port coupled to said source of pressurized aspirator gas, an outlet for coupling to a gas monitor, and a third port coupled to the outlet of said sub-sample tube from said adiabatic cooling chamber and means for alternatively selectively coupling said third port to said gas monitor and said aspirator gas inlet.

11. Apparatus as defined in claims 7, 8 or 9, wherein said cooling chamber has an inner cylinder covered with an insulating material, with said sub-sample tube axially aligned with and passing through said inner cylinder and the space between said inner cylinder and said sub-sample tube communicating with the cooling gas inlet and the cooling gas outlet.

12. A method for continuously withdrawing a gas sub-sample from a chamber containing a source of waste gas for introduction of the sub-sample to a gas monitor, comprising:

(a) withdrawing a sample of said waste gas from said waste gas chamber by use of a vacuum source exterior to said chamber;

(b) extracting a sub-sample of the sample waste gas prior to its entering the vacuum source;

(c) cooling said sub-sample below the ambient dew point so that condensate is removed therefrom;

(d) directing said cooled sub-sample of gas to a gas monitor for analysis of the gaseous components thereof.

13. A method as defined in claim 12 further comprising filtering out particulate matter from said sample gas prior to extraction of said sub-sample.

14. A method as defined in claim 13, wherein said vacuum source is an aspirator and vacuum therein is created by passing an aspirator gas through the aspirator.

15. A method as defined in claim 13, further comprising conducting the gas sample and aspirating gas back into said waste gas chamber.

16. A method as defined in claim 15, further comprising adiabatically expanding aspirating gas and using the expanded gas to cool the sub-sample prior to the sub-sample entering the aspirator.

17. A method as defined in claim 16, further comprising directing aspirating gas from a pressurized source of aspirator gas prior to expansion into a sub-sample tube which conducts said sub-sample and into a sample probe tube which conducts the gas sample and out into said waste gas chamber through a probe inlet located at an outlet of said sample probe tube in order to purge the tubes and probe inlet of accumulated particulate matter.

18. A method as defined in claim 17, further comprising shielding an inlet to said sample probe line from the direct flow of waste gas in said chamber.

* * * * *